United States Patent
De Mattia et al.

(10) Patent No.: US 10,101,144 B2
(45) Date of Patent: Oct. 16, 2018

(54) METHOD FOR DETECTING A STRAND GAP IN FIBER FABRIC AND A DEVICE FOR ITS IMPLEMENTATION

(71) Applicant: Airbus Operations S.A.S., Toulouse (FR)

(72) Inventors: Denis De Mattia, Basse Goulaine (FR); Christian Vivier, Saint Mars de Coutais (FR)

(73) Assignee: Airbus Operations S.A.S., Toulouse (FR)

( * ) Notice: Subject to any disclaimer, the term of this patent is extended or adjusted under 35 U.S.C. 154(b) by 297 days.

(21) Appl. No.: 14/859,714

(22) Filed: Sep. 21, 2015

(65) Prior Publication Data

US 2016/0091296 A1    Mar. 31, 2016

(30) Foreign Application Priority Data

Sep. 25, 2014   (FR) ..................... 14 59054

(51) Int. Cl.
  *G01B 7/14* (2006.01)
  *G01N 27/02* (2006.01)
  *G01N 27/90* (2006.01)

(52) U.S. Cl.
  CPC ............... *G01B 7/14* (2013.01); *G01N 27/02* (2013.01); *G01N 27/902* (2013.01)

(58) Field of Classification Search
  CPC ........ G01L 1/142; G01N 21/31; G01N 27/82; G01R 33/04; G01R 33/28
  USPC ........... 324/600, 200, 654, 207.22, 213–225, 324/239–247, 529, 500, 76.11, 76.15
  See application file for complete search history.

(56) References Cited

U.S. PATENT DOCUMENTS

| 2004/0124087 | A1 | 7/2004 | Christ et al. |
| 2005/0128095 | A1* | 6/2005 | Frazier .................... B61B 12/06 340/635 |
| 2008/0174306 | A1 | 7/2008 | Brady |
| 2009/0033323 | A1 | 2/2009 | Georgeson et al. |

FOREIGN PATENT DOCUMENTS

EP   1 387 166 A2   2/2004

OTHER PUBLICATIONS

French Search Report dated May 19, 2015 (FR 14 59054).
C. W. Davis et al: "Combined Investigation of Eddy Current and Ultrasonic Techniques for Composite Materials NDE" In: "Review of Progress in Quantitative Nondestructive Evaluation", Jan. 1, 1995 (Jan. 1, 1995), Springer US, Boston, MA, XP055189650, ISBN: 978-1-46-151987-4 pp. 1295-1301, DOI: 10.1007/978-1-4615-1987-4 165, * p. 1296, alinea 7 *—* page 1298, alinea 2 * * p. 1299, alinea 3; figures 3,5 *.

(Continued)

*Primary Examiner* — Melissa Koval
*Assistant Examiner* — Trung Nguyen
(74) *Attorney, Agent, or Firm* — Lerner, David, Littenberg, Krumholz & Mentlik, LLP

(57) ABSTRACT

A method for detecting a spacing defect between two adjacent strands of a layer of a fiber fabric includes positioning of the fiber fabric on a metal plate, the fiber fabric covered by an air-tight casing, removing air from between the metal plate and the casing, displacing an inductive sensor relative to the fiber fabric and identifying a defect based on a signal generated by the inductive sensor.

15 Claims, 3 Drawing Sheets

(56) References Cited

OTHER PUBLICATIONS

Pauli Vaara et al: "Technology Survey on NDT of Carbon-fiber Composites", Jan. 1, 2012 (Jan. 1, 2012), XP055189570, Extrait de l'Internet: URL:http:i/theseus32-kk.lib.helsinki.fi/bi tstreamjhandle/10024/54515/vaaraleinonen B 8 2012.pdf?sequence=1 [extrait le May 18, 2015] * pp. 25-27 *.

Martin H Schulze et al: "High-resolution eddy current sensor system for quality assessment of carbon fiber materials," Microsystem Technologies ; Micro and Nanosystems Information Storage and Processing Systems, Springer, Berlin, DE, vol. 16, No. 5, Feb 12, 2010 (Feb. 12, 2010), pp. 791-797, XP019804476, ISSN: 1432-1858.

Henning Heuer et al: "International Workshop Smart Materials, Structures & NDT in Aerospace Eddy Current Testing of Carbon Fiber Materials by High Resolution Directional Sensors," Nov. 4, 2011 (Nov. 4, 2011), XP055189722, Extrait de l'Internet: URL:http:jjw-ww.ndt.netjeventsjNDTCanada201 1/proceedingsjpapers/94 Heuer Rev1.pdf [extrait le May 18, 2015].

\* cited by examiner

METHOD FOR DETECTING A STRAND GAP IN FIBER FABRIC AND A DEVICE FOR ITS IMPLEMENTATION

BACKGROUND OF THE INVENTION

The invention relates to a method for detecting a gap between strands in fiber fabric and a device for its implementation.

Fiber fabrics are used in the manufacture of composite material parts.

Fiber fabric consists of several layers of fibers stacked on top of one another and sewn together. Each layer of fibers comprises a plurality of juxtaposed and parallel strands. As an order of magnitude, a strand has a width of approximately 3 mm and thickness of approximately 0.25 mm. Finally, each strand comprises a plurality of juxtaposed fibers.

Generally speaking, fiber fabric is in the form of a long strip having a width in the order of 1400 mm and a length of several tens of meters, for example. For the remainder of the description, the longitudinal direction corresponds to the length of the strip. This longitudinal direction is parallel to the X axis in FIGS. 1, 2A and 2B.

According to an configuration illustrated in FIG. 1, a fiber fabric 10 is said to be multiaxial and includes several layers, each layer having its own orientation, e.g. a first layer 12 with fibers oriented at 90° which are arranged perpendicularly to the longitudinal direction, a second layer 14 with fibers oriented at +45° which form an angle of +45° with the longitudinal direction, a third layer 16 with fibers oriented at 0°, which are arranged parallel to the longitudinal direction and a fourth layer 18 with fibers oriented at −45° which form an angle of −45° with the longitudinal direction.

Each layer of fibers must have a homogeneous surface density of fibers regardless of the size of the reference surface area so as to obtain a composite material part that is in compliance with the mechanical requirements. For example, the fiber surface density of a layer of carbon fibers is 270 g/m$^2$ for a thickness of approximately 0.25 mm.

As illustrated in FIG. 2A, to obtain a homogeneous fiber surface density, the strands 20 of the layer are juxtaposed, rectilinear and parallel to one another. Thus, the spacing between two adjacent strands must be constant over their entire length.

As illustrated in FIG. 2B, a layer of fibers comprises a defect 22, with two adjacent strands 24 and 24' being spread apart over a length L with a maximum distance d. The strands overlap on either side of the defect 22. Thus, this fiber layer has a heterogeneous fiber surface density with above-average surface density in the areas where the fibers overlap and a below-average fiber surface density between the spread fibers 24 and 24'.

A composite part containing such fabric will contain a defect. If this defect is located near a drill hole, the overlapping fibers may be severed during the drilling operation, while some of them would not have been cut had they not been overlapping. The cutting of additional fibers leads to a weakness in the composite material part.

To limit the risk of weakening composite material parts, the gap between two adjacent strands of the same layer must remain below a given threshold in the order of 2 mm.

According to a procedure, the process for manufacturing multiaxial fabric comprises the following steps.

For the fiber layers oriented at 90°, +45°, and −45°, for each layer, the strands are cut according to the width of the multiaxial fabric, then they are arranged by an automatic manipulator on a production line conveyor which advances the fabric. Following this removal step, it is possible to correct any gaps between the strands. The ends of the strands of layers at 90°, +45° and −45° are then maintained by clamps arranged on either side of the conveyor. These clamps exert a slight traction on the strands and hold them in position until the layers are sewn together at a stitching station. For this purpose, the movement of the clamps is synchronized with that of the conveyor.

As the strands of the layers at 90°, +45° and −45° are maintained under tension up to the stitching station, the risk of a spacing greater than 2 mm between the strands is negligible.

It is a different situation for the strands of layers with fibers oriented at 0°.

The length of these strands, which are oriented in the longitudinal direction, is equal to that of the strip of the multiaxial fabric which can reach several hundred meters. Each strand oriented at 0° is maintained straight solely by the tension applied to it between two points, one in the zone where the strand enters the production line and the other at the stitching station.

Given the distance separating these two points (in the order of 20 to 30 m) and the slight amount of tension exerted on the strands, it is possible that, as the layers move toward the stitching station, that this tension drops on one of the strands oriented at 0° and no longer maintains its tension. As the strand is initially wound, it tends to lose its straightness. Consequently, its spacing from the adjacent strand may exceed 2 mm. When the tension returns, the latter is too weak to again tighten the previously slack strand in a rectilinear manner. Thus, owing to existing friction between said strand and the strands of the adjacent layers, for example, the slack strand maintains its position and its spacing with an adjacent strand of the same layer, which can be greater than 2 mm.

Due to the nature of the manufacturing process, the risks of spacing in excess of 2 mm between two adjacent strands of a layer at 0° are non-zero.

Consequently, a defect such as this in a multiaxial fabric must be detected before it is used in a process to manufacture a composite material part.

A visual inspection is sufficient when the layer at 0° is visible. However, this layer at 0° is generally inserted between other layers and is not visible.

BRIEF SUMMARY OF THE INVENTION

An aspect of the invention aims to provide a method for detecting a strand gap in a fiber fabric to prevent fabric, having spacing between two adjacent strands greater than a given threshold, from being rejected and from being used to manufacture a composite material part.

For this purpose, the invention relates to a method for detecting a spacing defect between two adjacent strands of a layer of a fiber fabric. This method is characterized in that it comprises the following steps:

displacement of an inductive sensor relative to the fiber fabric, identification of a defect based on a signal generated by the inductive sensor.

Preferably, a defect is identified when the signal generated by the inductive sensor varies beyond a set range.

When the zone of the fiber fabric has a defect in the electromagnetic field produced by the inductive sensor, the fiber surface density varies so much that the disturbance generated by the fabric on the electromagnetic field varies and is no longer constant. Consequently, the value of the signal generated by the inductive sensor varies. When the value is outside the set range, the defect is not acceptable and the zone of the fiber fabric is deemed non-compliant.

According to another characteristic, the fiber fabric is positioned between the inductive sensor and a metal plate. This configuration promotes defect detection.

According to another characteristic, the fiber fabric is positioned on the metal plate and it is covered with an air-tight casing; the air between the metal plate and the casing is then removed. This configuration allows the fiber fabric to be pressed flat against the metal plate.

According to another characteristic, the inductive sensor comprises an end face from which an electromagnetic field is generated and it is moved so that its end face is in contact and slides on the casing. This configuration allows the end face of the inductive sensor to be placed as close as possible to a possible defect.

According to another characteristic, the inductive sensor is moved in a direction perpendicular to the deposit direction. This configuration allows a more sudden variation of the signal to be obtained in the event a defect is detected.

According to another characteristic, the inductive sensor is moved in at least one course which extends from one edge of the fiber fabric to the other. Advantageously, the inductive sensor moves in several courses spaced at a pitch of 500 mm.

The invention also relates to a device for detecting a spacing defect between two adjacent strands of a layer of a fiber fabric. This device is characterized in that it comprises a inductive sensor, a mechanism for moving the inductive sensor relative to the fiber fabric, and a system for identifying a defect based on a signal generated by the inductive sensor.

According to another characteristic, the mechanism for moving the inductive sensor comprises a crosspiece positioned above the fiber fabric, perpendicular to the deposit direction, a carriage which supports the inductive sensor and which is movable along the crosspiece.

Preferably, the device comprises a connection between the inductive sensor and the carriage configured to allow a clearance of the inductive sensor relative to the carriage in a direction parallel to a detection axis of the inductive sensor, said connection comprising a spring arranged so as to push the inductive sensor towards of the fiber fabric.

According to a first embodiment, the device comprises a metal plate on which the fiber fabric is positioned.

Preferably, it comprises a portal structure consisting of two uprights arranged on either side of the fiber fabric and supporting the crosspiece. Preferably, this portal structure can pivot.

Advantageously, it comprises an air-tight casing, connected to the two uprights in a hermetic manner.

According to another characteristic, the metal plate is perforated and the device comprises a vacuum system connected to a chamber closed by said perforated metal plate.

According to a second embodiment, the device comprises two conveyor belts between which is placed the fiber fabric to be inspected.

Preferably, it comprises:
 a first belt conveyor which comprises a perforated metal strip positioned under the fiber fabric and a vacuum chamber positioned under the metal strip, and/or
 a second conveyor belt which comprises a plastic film, positioned on the fiber fabric.

BRIEF DESCRIPTION OF THE DRAWINGS

Other features and advantages will become apparent from the following description, given by way of example only, with reference to the accompanying drawings in which.

DETAILED DESCRIPTION

Figure 4:
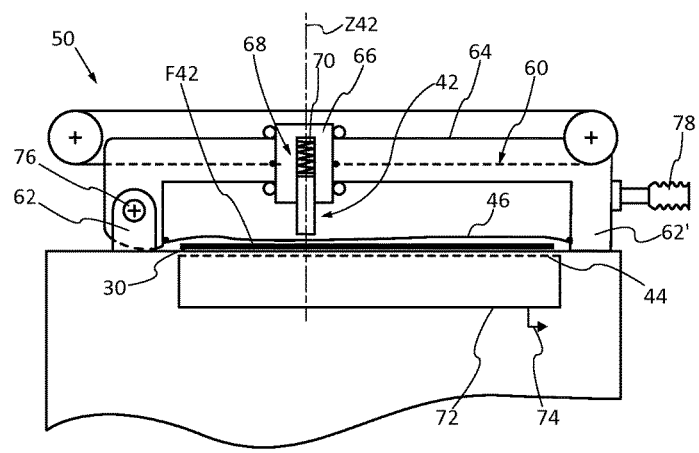
FIG. 4 is a side view of the device illustrated in FIG. 3.
Figure 5:
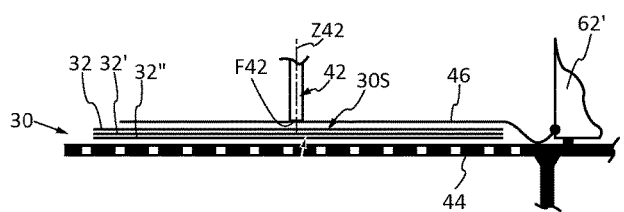
FIG. 5 is a sectional view illustrating a detail of FIG. 4.
Figure 6:
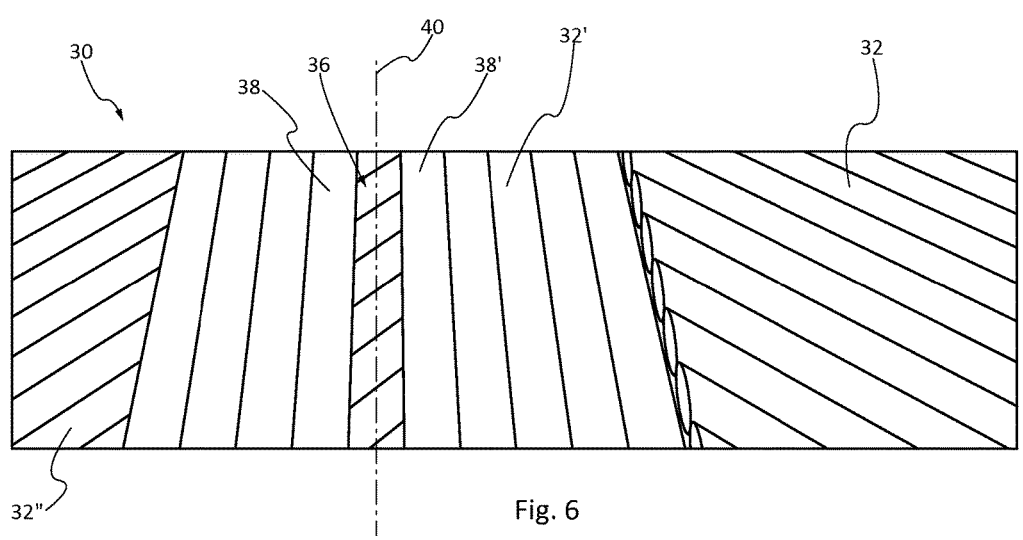
FIG. 6 is a perspective view of an example of a fabric with a defect.

A fiber fabric 30 is represented in FIGS. 4 to 6. This fiber fabric comprises several layers 32, 32', 32". In a known manner, each layer comprises a plurality of rectilinear strands, juxtaposed and parallel to each other. Each strand comprises at least one fiber, preferably several fibers juxtaposed between them.

The fiber fabric 30 comprises a lower surface 30I and an upper surface 30S.

In order for the fabric to be deemed compliant, two adjacent strands of the same layer must be uniformly spaced over their entire length. As the strands are juxtaposed, this spacing must not exceed a given threshold in the order of 2 mm.

Figure 1:
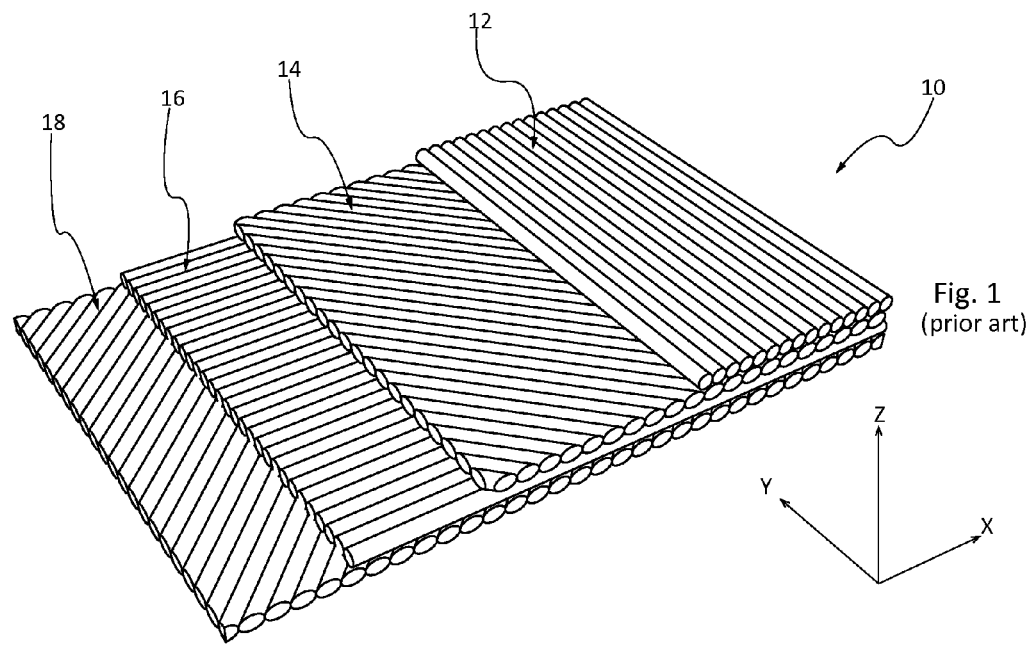
FIG. 1 is a perspective view of a portion of a multiaxial fabric showing layers with different orientations according to prior art.
Figure 2A:
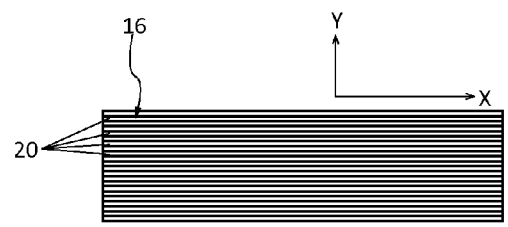
FIG. 2A is a top view of a layer of a multiaxial fabric that is free of defects.
Figure 2B:
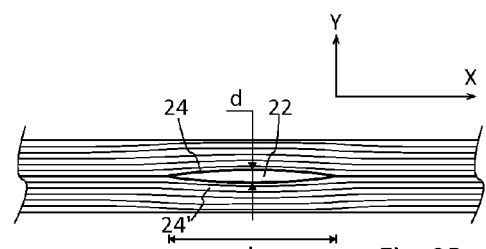
FIG. 2B is a top view of a layer of a multiaxial fabric having a defect.

For example, the fiber fabric 30 is identical to that of the prior art described in FIG. 1. The layer 32 corresponds to a layer with strands oriented at +45°, layer 32' corresponds to a layer with strands oriented at 0° and layer 32" corresponds to a layer with strands oriented at −45°.

FIG. 6 represents a defect 36 that corresponds to a gap between two adjacent strands 38, 38' above the given threshold. These adjacent strands 38, 38' belong to a layer whose strands are oriented in a deposit direction shown by the arrow 40.

For example, the adjacent stands 38, 38' belong to the layer 32' whose strands are oriented at 0°. In this case, the deposit direction 40 is parallel to the longitudinal direction.

The layer having the defect 36 is separated from the upper surface 30S by at least one other layer and the lower surface 30I by at least one other layer. Consequently, the layer with the defect 36 is not visible.

The fibers of the fiber fabric 30 are made of carbon. More generally, they are made of an electrically conductive material.

The method for detecting a spacing defect in a fiber fabric comprises the following steps:
 displacement of an inductive sensor 42 relative to the fiber fabric 30,
 identification of a defect based on a signal generated by the inductive sensor 42.

Preferably, a defect is identified when the signal generated by the inductive sensor 42 varies beyond a set range. The fixed range is determined based on the given threshold that corresponds to the spacing between two adjacent strands, beyond which the fiber fabric is considered non-compliant.

The inductive sensor 42 comprises a detection zone. It is moved near the upper surface 30S or the lower surface 30I so that the layer, the mesh spacing of which is being inspected, is disposed in the sensing field of the inductive sensor 42.

The inductive sensor 42 is of analog type. It generates an electromagnetic field. When the inductive sensor is disposed above a zone of the fiber fabric without defects, the electromagnetic field generated by the inductive sensor 42 is disturbed in some way and the signal generated by the inductive sensor 42 has a certain value. As long as the zone of the fabric present in the magnetic field of the inductive sensor does not have a defect, the layers each having a homogenous fiber surface density, the disturbance generated by the fabric on the electromagnetic field is constant and the value of the signal generated by the inductive sensor is substantially constant. When the zone of the fiber fabric has a defect in the electromagnetic field produced by the inductive sensor 42, the fiber surface density of at least one layer varies to an extent that the disturbance generated by the fabric on the electromagnetic field varies and is no longer constant. Consequently, the value of the signal generated by the inductive sensor varies. When the value is outside the set range, the defect 36 is not acceptable and the zone of the fiber fabric is deemed non-compliant.

According to an embodiment illustrated in FIG. 5, the inductive sensor 42 is cylindrical with a detection axis Z42 and comprises an end face F42 perpendicular to the detection axis Z42 from which the electromagnetic field is generated.

To improve defect detection, the fiber fabric 30 to be inspected is positioned between a metal plate 44 and the inductive sensor 42. Advantageously, the fiber fabric 30 to be inspected is pressed against the metal plate 44. In this configuration, the lower surface 30I is pressed against the metal plate 44 and the inductive sensor 42 moves just above the upper surface 30S.

Preferably, the fiber fabric 30 is covered by an air-tight casing 46 which is connected in a hermetic manner with the metal plate 44. The metal plate comprises at least one orifice connected to a vacuum system to remove air between the metal plate 44 and the casing 46. Thus, the fiber fabric 30 is pressed against the metal plate 44 and the casing 46 against the fiber fabric 30.

Preferably, the end face F42 of the inductive sensor 42 is placed in contact with the casing 46. The inductive sensor 42 thus moves slidably on the casing 46 without displacing the fibers and the strands of the fiber fabric. This configuration allows the inductive sensor 42 to move as close as possible to the fiber fabric 30 which provides superior detection of any defects.

In a first configuration, the fiber fabric 30 is fully covered by the casing 46 which is connected in a hermetic manner, directly or indirectly, to the metal plate 44 over the entire periphery of the fiber fabric 30.

According to another configuration, the fiber fabric 30 is a strip of fiber fabric. In this case, the envelope 46 covers only a portion of the strip of fiber fabric. It is directly or indirectly connected in a hermetic manner, on either side of the strip, to the metal plate 44 to obtain a localized vacuum, notably in the defect detection zone.

According to another characteristic, the inductive sensor 42 is moved along a detection direction perpendicular to the deposit direction 40 of the layer, for which the mesh spacing is being inspected.

In the case of a fiber fabric in the form of a strip comprising a layer of strands oriented at 0°, i.e. longitudinally, the inductive sensor 42 moves transversely, i.e. perpendicularly to the longitudinal direction. In this configuration, the inductive sensor 42 moves along at least one course which extends over the entire width of the band, from one edge of the fiber fabric 30 to the other and which is perpendicular to the deposit direction 40.

According to another characteristic, the sensor 42 follows several courses, parallel with each other and spaced at a pitch of approximately 500 mm.

Insofar as the spacing between two strands extends over distances greater than 1 m, an inspection every 500 mm allows a compromise to be achieved between the speed of the inspection and the certainty to detect defects.

Figure 7A:
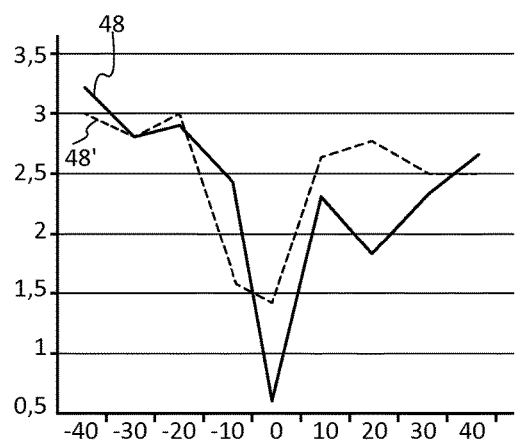
FIG. 7A is a diagram representing an electrical characteristic that varies in the presence of a defect in a first configuration.

FIG. 7A represents a signal 48 generated by the inductive sensor 42, this signal 48 corresponding to an electric current according to the position of the inductive sensor which moves to either side of the defect along a first course.

FIG. 7A also shows a signal 48' generated by the inductive sensor 42 upon detection of the same defect as for the signal 48, but according to another course.

Figure 7B:
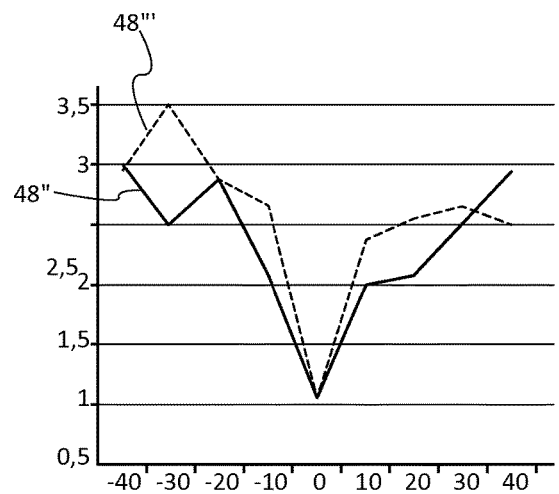
FIG. 7B is a diagram representing an electrical characteristic that varies in the presence of a defect in a second configuration.

FIG. 7B illustrates two signals 48", 48''' generated by the inductive sensor 42 upon detection of the same defect as for the signal 48, the layer at 0° being positioned in the second position from the top in FIG. 7A and in the third position for FIG. 7B.

Thus, regardless of the position of the layer to be inspected, the method of the invention allows a spacing defect between the strands to be identified.

According to a first procedure, the fiber fabric 30 is inspected on a specific detection device 50 (visible in FIGS. 3 to 6) before being used in a process for manufacturing composite material parts.

According to an embodiment, the fiber fabric 30 is in the form of a strip that is generally stored on a roller.

Figure 3:
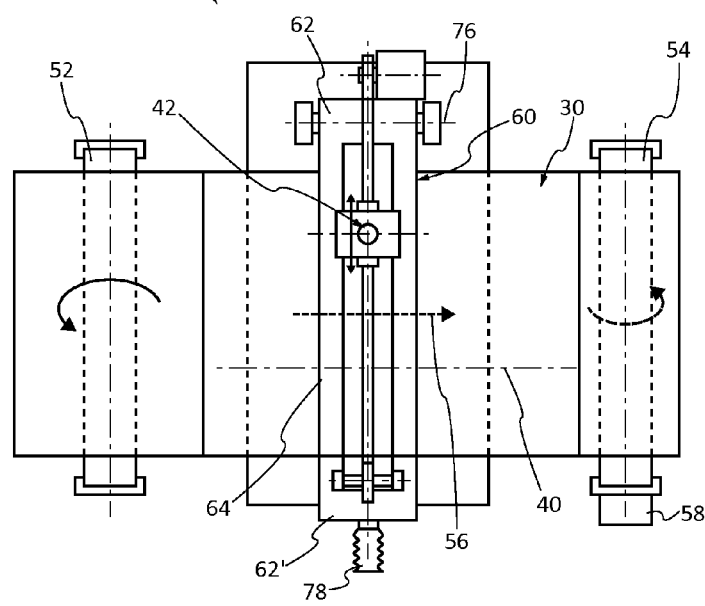
FIG. 3 is a top view of a defect detection device that illustrates a first embodiment of the invention.

As illustrated in FIG. 3, according to a first embodiment, the detection device 50 comprises a frame supporting a metal plate 44 on which the fiber fabric 30 is placed. This fiber fabric is initially wound on a first roller 52. The fiber fabric 30 is unwound from the first roller 52 to be wound onto a second roller 54. The scrolling direction of the strip of fiber fabric between the first roller 52 and the second roller 54 is indicated by the arrow 56.

The rollers 52 and 54 are disposed on either side of the metal plate 44. The axes of rotation of rollers 52 and 54 are perpendicular to the longitudinal direction.

Preferably, a motor unit 58 is provided on the second roller 54 to scroll the fiber fabric over the metal plate 44 from the first roller 52 to the second roller 54. The motor unit 58 allows the fiber fabric 30 to be scrolled step-by-step.

Alternatively, the strip of fiber fabric 30 can be scrolled manually.

The detection device 50 comprises a portal structure 60 with two uprights 62, 62' which are arranged on either side of the fiber fabric strip and which support a crosspiece 64 arranged above the metal plate 44. The crosspiece 64 is positioned perpendicular to the deposit direction 40 and parallel to the metal plate 44.

The detection device 50 also comprises a carriage 66 which supports an inductive sensor 42 and which is movable along the crosspiece 64 in a transverse direction, or in a direction perpendicular to the strands, the spacing of which is inspected.

The course of the carriage 66 on the crosspiece has a length such that the inductive sensor 42 moves from one side of the strip of fiber fabric 30 to the other.

Preferably, the displacement of the carriage 66 along the crosspiece is motorized. Alternatively, it can be displaced manually.

The inductive sensor 42 is connected to the carriage 66 by a connection. Advantageously, this connection allows the spacing between the end face F42 of the inductive sensor and the metal plate 44 to be adjusted.

According to an embodiment illustrated in FIG. 4, the inductive sensor 42 is connected to the carriage 66 by a connection 68 which allows a small amount of deviation of the inductive sensor relative to the carriage 66 along a direction parallel to the detection axis Z42 of the inductive sensor (i.e. perpendicular to the metal plate 44). The connection 68 between the inductive sensor 42 and the carriage 66 comprises a spring 70 arranged so as to push the inductive sensor 42 towards the fiber fabric 30. This configuration allows the inductive sensor 42 to always be positioned against the fiber fabric 30, more precisely against the casing 46.

According to an embodiment, the metal plate 44 is perforated and comprises a plurality of holes distributed over its entire surface. In addition, the detection device 50 comprises a chamber 72 closed by the perforated metal plate 44 and connected to a vacuum system 74.

The detection device 50 also comprises an air-tight casing 46 which is connected in a hermetic manner to the two uprights 62 and 62' of the portal structure 60 and which cover the fiber fabric 30 above the metal plate 44.

According to an embodiment illustrated in FIGS. 3 and 4, the portal structure 60 pivots. For this purpose, one of the uprights 62 is connected to the frame of the device by a pivoting connection comprising an axis of rotation 76 parallel to the longitudinal direction. Thus, the other upright 62' can be moved away from the frame to release the casing 46 from the fiber fabric 30 and allow it to be placed under the portal structure or be scrolled. This upright 62' preferably comprises a handle 78 used to pivot the portal structure 60.

The operating principle of the detection device 50 will now be described.

The first roller 52, containing the strip of fiber fabric 30 to be inspected, is put into place. Next, the strip is unwound and placed between the metal plate 44 and the casing 46. After creation of the vacuum, the fiber fabric 30 is pressed against the metal plate 44 and the casing 46 is pressed against the fiber fabric 30. The inductive sensor 42 is positioned in contact with the casing 46 and one side of the strip of fiber fabric. The carriage 66 is moved in translation until the inductive sensor 42 reaches the other edge of the strip. During this movement, a signal 48 is generated by the inductive sensor 42. If there is no defect, the signal 48 is substantially constant. When the inductive sensor 42 is in plumb with a defect, the signal 48 varies significantly.

When the entire width of the strip of fiber fabric was examined, the inductive sensor 42 and casing 46 assembly is released by pivoting the portal structure 60 so as to advance the strip of fiber fabric 30 by one step. As stated previously, the pitch between two adjacent courses is of the order of 500 mm.

Once the strip of fiber fabric 30 has been moved, the portal structure 60 is returned to its initial position so that the casing 46 is in contact with the fiber fabric 30 and the inductive sensor 42 in contact with the casing 46. The carriage 66 is again moved in translated so that the inductive sensor 42 moves from one side of the strip of fiber fabric 30 to the other.

These various steps are repeated until the entire strip of fiber fabric has been examined.

Figure 8:
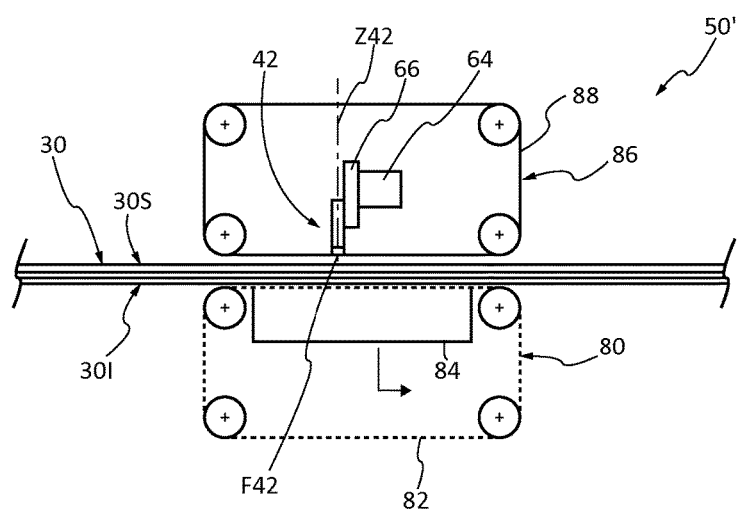
FIG. 8 is a side view of a defect detection device that illustrates a second embodiment of the invention.

According to a second procedure shown in FIG. 8, the fiber fabric 30 is inspected on the production line. In this case, a detection device 50' is integrated in the fiber fabric production line. Preferably, it is placed after the stitching station. According to this procedure, the strip of fiber fabric moves continuously, contrary to the first procedure which uses step-by-step scrolling.

According to a second embodiment illustrated in FIG. 8, a detection device 50' comprises two conveyor belts between which the strip of fiber fabric 30 to be inspected is positioned. A first conveyor belt 80 is positioned under the strip of fiber fabric 30 and comprises a perforated metal strip 82. This metal strip 82 is in contact with the lower surface 30I of the fiber fabric 30 and passes above a vacuum chamber 84. The periphery of this vacuum chamber 84 comprises a seal so as to obtain an air-tight seal between said chamber 84 and the perforated metal strip 82.

A second conveyor belt 86 is positioned on the strip of fiber fabric 30 and comprises a plastic film 88 in contact with the upper surface 30S of the fiber fabric 30. When the vacuum is established, the part of the plastic film 88 located above the vacuum chamber 84 presses the fiber fabric 30 against the perforated metal strip 82. In addition, as previously, the detection device 50' comprises a crosspiece 64, a carriage 66 and an inductive sensor 42 substantially identical to those of the first embodiment.

The scrolling speeds of the two conveyor belts 80 and 86 are synchronized with that of the fiber fabric 30.

According to this second procedure, the inductive sensor 42 moves from one side of the strip of fiber fabric 30 to the other, perpendicular to the scrolling direction of said strip, in a continuous manner to sweep said strip.

According to the two embodiments, the detection device 50 or 50' comprises a system for identifying a defect based on a signal generated by the inductive sensor.

Preferably, the identification system is configured to identify a defect if the signal generated by the inductive sensor varies beyond a set range.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method of detecting a spacing defect between two adjacent strands of a layer of a fiber fabric, said strands being placed according to a deposit direction, wherein the method comprises:
   positioning of the fiber fabric on a metal plate, said fiber fabric being covered by an air-tight casing;
   removing air from between the metal plate and the casing;
   displacing an inductive sensor, supported by a carriage, relative to the fiber fabric, the carriage being movable along a crosspiece positioned above the fiber fabric perpendicular to the deposit direction, the inductive sensor and the carriage configured, via a connection, to allow a clearance of the inductive sensor relative to the carriage in a direction parallel to a detection axis of the inductive sensor, said connection comprising a spring arranged so as to push the inductive sensor towards the fiber fabric; and identifying, by an identification system, a defect based on a signal generated by the inductive sensor.

2. The method according to claim 1, wherein a defect is identified when the signal generated by the inductive sensor varies beyond a set range.

3. The method as claimed in claim 1, wherein the inductive sensor comprises an end face from which an electromagnetic field is generated, and wherein the inductive sensor is moved so that the end face is in contact and slides on the casing.

4. The method as claimed in claim 1, wherein the inductive sensor is moved in a direction perpendicular to the deposit direction.

5. The method as claimed in claim 4, wherein the inductive sensor is moved in at least one course extending from one edge of the fiber fabric to the other.

6. The method as claimed in claim 5, wherein the inductive sensor moves in several courses spaced at a pitch of 500 mm.

7. A device for detecting a spacing defect between two adjacent strands of a layer of a fiber fabric, said strands being deposited along a deposit direction, the device comprising:

a metal plate adapted to allow the fiber fabric to be positioned on said metal plate;

an air-tight casing adapted to be positioned on the fiber fabric;

a vacuum system to remove air from between the metal plate and the casing;

an inductive sensor;

a mechanism for moving the inductive sensor relative to the fiber fabric, the mechanism to move the inductive sensor comprising:

a crosspiece positioned above the fiber fabric perpendicular to the deposit direction; and a carriage supporting the inductive sensor and movable along the crosspiece;

a system for identifying a defect based on a signal generated by the inductive sensor; and a connection between the inductive sensor and the carriage configured to allow a clearance of the inductive sensor relative to the carriage in a direction parallel to a detection axis of the inductive sensor, said connection comprising a spring arranged so as to push the inductive sensor towards the fiber fabric.

8. The device as claimed in claim 7, wherein the mechanism to move the inductive sensor comprises:

a crosspiece positioned above the fiber fabric perpendicular to the deposit direction; and a carriage supporting the inductive sensor and movable along the crosspiece.

9. The device as claimed in claim 7, further comprising a portal structure comprising first and second uprights arranged on either side of the fiber fabric and supporting the crosspiece.

10. The device as claimed in claim 9, wherein the air-tight casing is connected in a hermetic manner to the first and second uprights.

11. The device as claimed in claim 9, wherein the portal structure pivots.

12. The device as claimed in claim 7, wherein the metal plate is perforated, and wherein the vacuum system is connected to a chamber closed by said perforated metal plate.

13. The device as claimed in claim 7, further comprising first and second conveyor belts between which is positioned the fiber fabric to be inspected.

14. The device as claimed in claim 13, further comprising a first conveyor belt comprising a perforated metal strip positioned under the fiber fabric and a vacuum chamber positioned under the metal strip.

15. The device as claimed in claim 13, further comprising a second conveyor belt comprising a plastic film, positioned on the fiber fabric.

* * * * *